United States Patent [19]

Flynn

[11] Patent Number: 4,903,523

[45] Date of Patent: Feb. 27, 1990

[54] TEST OBJECT AND METHOD OF CHARACTERIZATION OF AN ULTRASONIC BEAM AND ITS SIDE LOBES

[76] Inventor: John J. Flynn, 5435 Sixth Ave., Los Angeles, Calif. 90043

[21] Appl. No.: 97,599

[22] Filed: Sep. 16, 1987

Related U.S. Application Data

[63] Continuation-in-part of Ser. No. 775,754, Sep. 13, 1985, abandoned.

[51] Int. Cl.⁴ ............... G01D 18/00; G01B 15/00; A61B 8/00; G09B 23/14
[52] U.S. Cl. ..................... 73/1 DV; 73/1 R; 128/660.01
[58] Field of Search ............ 73/1 DV, 1 R; 128/660, 128/660.01, 916; 367/13

[56] References Cited

U.S. PATENT DOCUMENTS

| | | | |
|---|---|---|---|
| 4,331,021 | 5/1982 | Lopez et al. | 73/1 DV |
| 4,417,582 | 11/1983 | Trimmer et al. | 128/660 |
| 4,453,408 | 6/1984 | Clayman | 73/1 DV |
| 4,493,653 | 1/1985 | Robbins et al. | 128/660 X |
| 4,567,896 | 2/1986 | Barnea et al. | 73/1 R X |
| 4,704,892 | 11/1987 | Tarnai | 73/1 R X |
| 4,729,235 | 3/1988 | Podleeh | 73/1 DV |

OTHER PUBLICATIONS

"Slice Thickness Measurements", *J. Ultrasound Med.*, no. 7, pp. 48714 498, pub. Sep. 1988; Albert Goldstein, Ph.D.

A. Goldstein, "Quality Assurance in Diagnostic Ultrasound", Chapters 7 and 9.2, U.S. Dept. of Health and Human Services, FDA 81-8139 (Oct. 1980), pp. i-x & 1-66.

A. Goldstein, "Slice-Thickness Artifacts in Gray Scale Ultrasound", Journal of Clinical Ultrasound, 9:365-375 (Sep. 1981).

*Primary Examiner*—Tom Noland
*Attorney, Agent, or Firm*—Lyon & Lyon

[57] ABSTRACT

A test object for use in determining the accuracy of and to calibrate ultrasonic scanning equipment is disclosed. The test object provides for the determination of elevational resolution. Additionally, the test object provides for the determination of the existence, location, intensity and width of side lobes, both substantially in the direction of the scanning plane and in substantially the direction normal to the scanning plane.

11 Claims, 7 Drawing Sheets

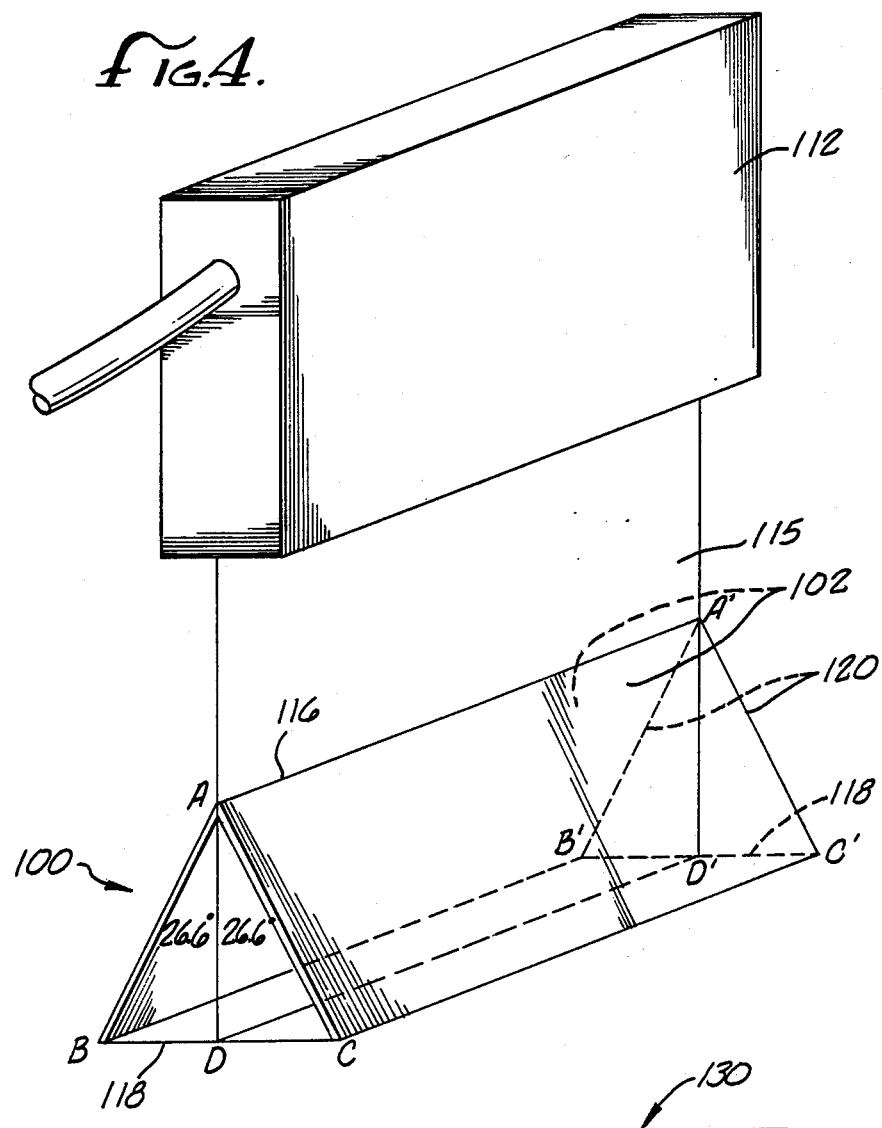
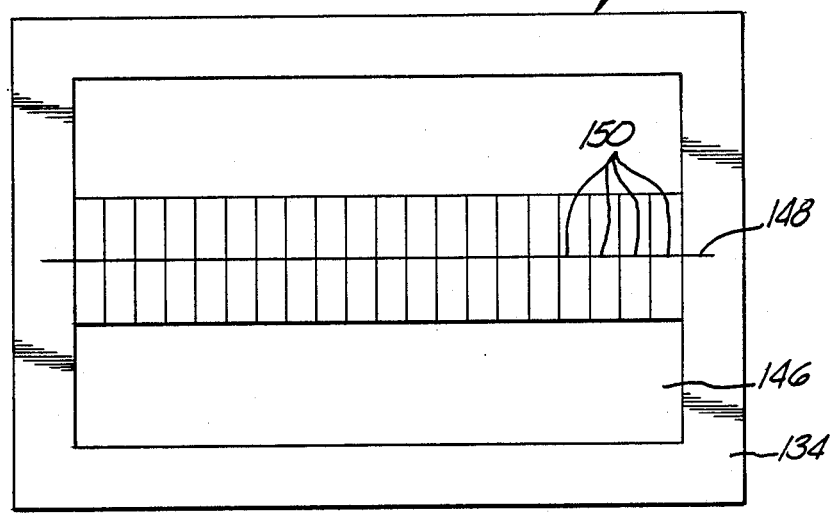

TEST OBJECT AND METHOD OF CHARACTERIZATION OF AN ULTRASONIC BEAM AND ITS SIDE LOBES

RELATED APPLICATIONS

This application is a continuation in part of application Ser. No. 775,754 filed Sept. 13, 1985 and now abandoned.

BACKGROUND OF THE INVENTION

1. Field of the Invention

The present invention relates generally to medical diagnosis and more particularly to the non-destructive testing and non-invasive examination of soft-tissue and body organs using ultrasonic diagnostic equipment. Specifically this invention is directed to a test object used to test the accuracy of and calibrate ultrasonic diagnostic equipment, such as pulse echo body scanners and the like, presently used by many hospitals and doctors.

2. Description of the Prior Art

Apparatus and techniques which permit the non-destructive testing and non-invasive examination of soft tissue and body organs are of particular interest to the medical community. Examples of presently available techniques include x-ray, nuclear medicine, thermography and diagnostic ultrasound. Ultrasonic diagnostic techniques are important because they offer a very high benefit to risk ratio for the patent and the ability to perform quality imaging of soft tissue organs. Thus ultrasonic diagnosis has found widespread applicability to the medical subfields of obstetrics, gynecology, cardiology, neurology, ophthalmology and urology among others. Ultrasonic diagnostic has proved of particular value as a diagnostic aid for the pregnant uterus including fetus and placenta, eye, breast, brain, lung, kidney, liver, gall bladder, bile ducts, pancreas, spleen, heart and blood vessels and soft tissues of extremities of neck including thyroid and parathyroid glands.

Ultrasonic diagnostic instruments operate on either a pulse-echo or Doppler principle. These principles are both well known. Most frequently the imaging of soft body tissue is accomplished using the pulse-echo principle. Short bursts of ultrasonic energy are transmitted into the body and the echoes are recorded. The time required for an emitted pulse to return as an echo provides an indication of the distance of a measured structure. Echoes occur at the boundaries between different tissues within the body since a fraction of the incident energy is deflected whenever the characteristic impedance of the structure under examination changes. Typically a change in the characteristic impedance occurs at such a boundary. Impedance is defined as the product of the density of the tissue multiplied by the velocity of sound. The first boundary will not typically reflect all the incident energy which may be reflected at subsequent boundaries. Thus, various boundaries at various depths can be observed.

Ultrasonic diagnostic equipment is used by a process called scanning. Scanning involves the movement of a pulsed sound beam propagated by a transducer through a plane. The transducer converts electrical signals into acoustic pulses. Through scanning a two-dimensional image of the various organs or body regions of interest are generated.

The quality of the two-dimensional image generated through the scanning process is dependent on the axial, lateral and elevational resolution of the transmitted ultrasonic beam and the absence or presence of side lobes. Resolution is also substantially dependent on the cross-section of the ultrasonic beam at various depths.

A known method of measuring the resolution of an ultrasonic beam employs measurement of the intensity of an ultrasonic beam using a hydrophone in an open tank of water at various depths in an engineering laboratory setting. This is impractical and not available in most clinical laboratories. For this reason, simple test objects have been devised in recent years to measure beam parameters.

A method and device for determining the axial and lateral resolution of the ultrasonic beam and the beam width in the direction of the scanning plan was adopted by the American Institute of Ultrasound in Medicine (AIUM) in 1974. The device involves the use of scanning targets immersed in an air-free scanning medium whose velocity of sound substantially corresponds to that of the soft body tissue being examined. Typically, the velocity of sound in human tissue is 1540 m/s. The construction and use of this device is fully described in chapters 7 and 9.2 of a Department of Health and Human Services publication, FDA 81-8139, in its Bureau of Radiological Health Quality Assurance Series entitled "Quality Assurance in Diagnostic Ultrasound—Manual for the Clinical User" authored by Albert Goldstein, Ph.D. and published in October, 1980. This document in its entirety is incorporated herein by reference.

Trimmer (U.S. Pat. No. 4,417,582) provides a device and method for measuring lateral resolution in the scanning plane which differ from the AIUM test object in that it allows for continuous measurements of lateral resolution rather than the discrete measurements that characterize the AIUM test object.

Clayman (U.S. Pat. No. 4,453,408) describes a device that produces a profile of the beam, thus providing for a continuous range of plane beam width measurements.

All of devices above are inadequate for determining the width of the ultrasonic beam in a direction substantially normal to the scanning plane, sometimes referred to as out-of-plane beam width "elevational resolution" or "slice thickness," an important measurement when the ultrasonic diagnostic equipment being used generates a non-circular beam cross-section. Additionally these devices do not provide for a method to determine the existence, location, width or intensity of side lobes in either substantially the direction of the scanning plane or in the direction substantially normal to the scanning plane.

SUMMARY OF THE INVENTION

Accordingly, it is the purpose of the present invention to provide a test object comprising an arrangement of scanning targets that provide for the determination of the ultrasonic beam width in the direction substantially normal to the scanning plane and the existence of side lobes both in substantially the direction of the scanning plane and in the direction substantially normal to the scanning plane in addition to the axial and lateral resolution of the ultrasonic beam and the beam width in the direction of the scanning plane.

BRIEF DESCRIPTION OF THE DRAWINGS

FIG. 4 is a perspective view of a single cluster of targets providing a continuous measurement of the slice thickness of the beam within a specified range.

FIG. 7 is a top view of the object depicted in FIG. 5.

DESCRIPTION OF THE PREFERRED EMBODIMENTS

Figure 1:
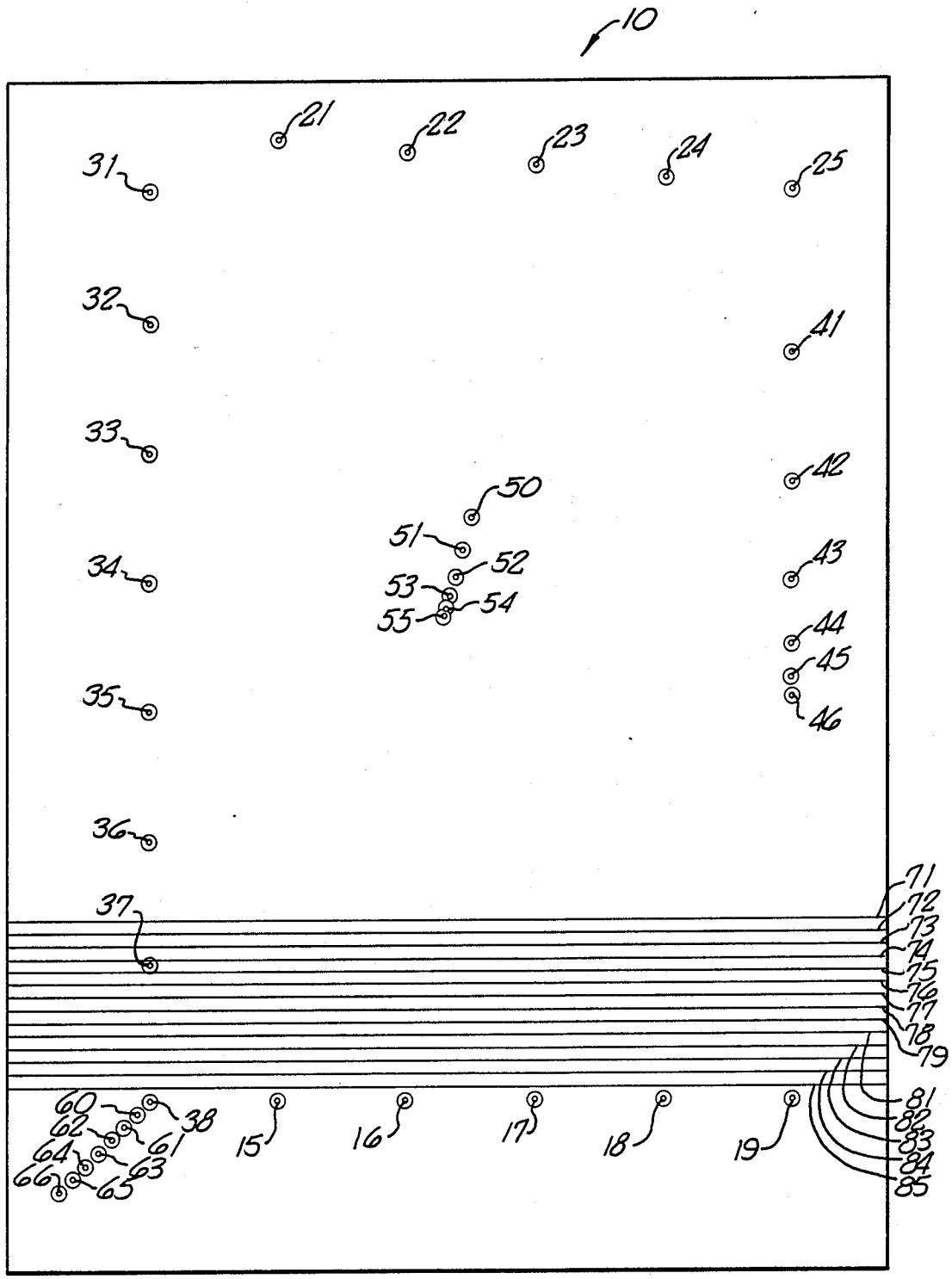
FIG. 1 is a side view, perpendicular to the scanning plane, of the AIUM test object modified in accordance with the present invention.

Referring to FIG. 1, a modified AIUM test object (10) is shown suitable for the determination of the axial and lateral resolution of the ultrasonic beam and the beam width in the direction of the scanning plane and in the direction substantially normal to the scanning plane. Additionally the test object is suitable for the determination of the existence, location, intensity or width of side lobes in substantially the direction of the scanning plane and in the direction substantially normal to the scanning plane. The size of the test object shown is for illustration only. The test object can be larger or smaller as required. For reference purposes (still referring to FIG. 1), the axial direction or depth of the beam is from top to bottom, the lateral direction or in-plane width of the beam is from side to side, and out-of-plane beam width extends normal to the plane of the figure.

An ultrasonic beam, not shown, is moved back and forth through the test object (10) in the direction of the scanning plane. A portion of the beam will be reflected if it intersects a scanning target thereby forming an echo that will be recorded by undepicted ultrasonic diagnostic equipment.

The scanning targets are generally rods or wires of stainless steel or nylon filaments or the like and should have a minimum cross-sectional area sufficient to create a measurable echo. Cylindrical rods having a 0.75 mm cross-section are satisfactory. The scanning targets are supported by affixing each end of the rod in an end plate of acrylic plastic or the like.

In use the test object (10) is generally immersed in an air-free medium whose velocity of sound corresponds to that of the tissues being examined. Water is a satisfactory medium and when used at a temperature of 47° C. closely corresponds to the average velocity of sound in tissue of 1540 m/s. Other mediums and their use are commercially available and are known in the art.

Scanning targets (15, 16, 17, 18, 19 and 38) are used for horizontal calibration and measurement of horizontal linearity. Scanning targets (21, 22, 23, 24 and 25) are used in the determination of the dead zone or ring down distance for the equipment being used. Scanning targets (31, 32, 33, 34, 35, 36, 37 and 38) are used for depth calibration and beam width in the direction of the scanning plane. Scanning targets (25, 41, 42, 43, 44, 45 and 46) are used to determine the lateral resolution of the ultrasonic beam in the direction of the scanning plane. Scanning targets (50, 51, 52, 53, 54 and 55) are used in the determination of axial resolution. The number of targets depicted is for illustration only; more or less targets can be used as required. The use of these scanning targets is known in the art. A detailed explanation of their use can be found in the AIUM publication previously referred to and which is incorporated herein by reference.

However it has not been known how to determine the width of the ultrasonic beam in a direction substantially orthogonal to the scanning plane nor how to determine the existence location or, intensity of side lobes in substantially the direction of the scanning plane or in the direction substantially normal to the scanning plane by means of a simple test object.

Scanning targets (60, 61, 62, 63, 64, 65 and 66) are used in the determination of the existence, location, intensity and width of side lobes substantially in the direction of the scanning plane. When the depth calibration of the transducer is being performed using scanning targets (31, 32, 33, 34, 35, 36, 37 and 38) the presence or absence, and characteristics if present, of a side lobe is determinable by using these scanning targets (60, 61, 62, 63, 64, 65 and 66).

The location for scanning targets (60, 61, 62, 63, 64, 65 and 66) is dependent on the ultrasonic diagnostic equipment being used. As a group, the targets should be positioned approximately where the location of a side lobe is predicted by well-known physical principles. From each other, the lateral spacing of the targets is preferably small, within construction limitations, for greater precision. The targets are axially displaced to allow for axial discrimination. The axial displacement of the targets is preferably as small as possible, but generally no smaller than the axial resolution of the equipment being used. Displacing the targets by 2 mm in the axial direction and 2 mm in the lateral directions is generally satisfactory for 1-3.5 megahertz equipment. For higher frequency equipment less spacing between the targets is generally required. This invention is not limited, in any way, to the number of targets shown. More or less targets can be used. More targets are likely to be used if it is necessary to determine the presence of second order or other higher orders of side lobes. Additionally, the targets can be moved up or down in the test object as required.

Figure 2:
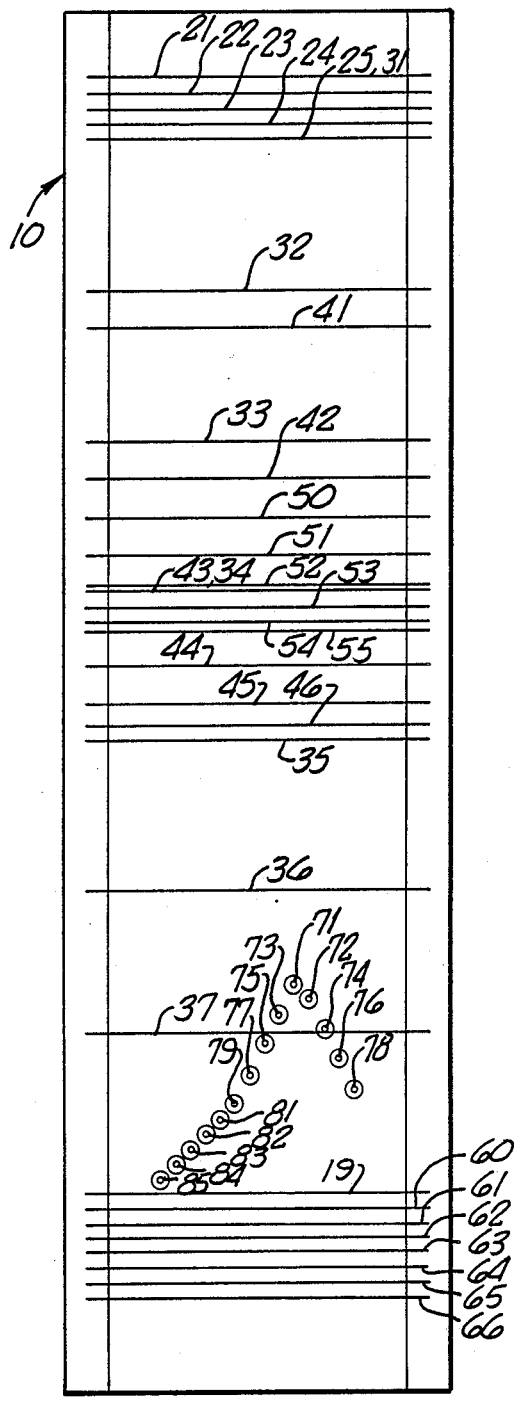
FIG. 2 is an end view of the test object depicted in FIG. 1.

Referring to FIG. 2, scanning targets (71, 72, 73, 74, 75, 76, 77, 78 and 79) are used in the determination of the width of the ultrasonic beam in a direction substantially normal to the scanning plane. As the ultrasonic beam is moved back and forth in the scanning plane centered to be coincident with the apices of the scanning targets some of the targets will produce an echo. The number of wires detected and echoes recorded will indicate the width of the scanning beam in the direction substantially normal to the scanning plane. The targets are axially displaced to provide for the counting of the number of targets that are intersected by the ultrasonic beam. The axial displacement of the targets is preferably as small as possible, but generally no smaller than the axial resolution of the equipment being used. Displacing the targets by 2 mm in the axial direction and 2 mm in the lateral direction from each other target is generally satisfactory for 1-3.5 megahertz equipment. As previously stated, less spacing between targets is preferred when higher frequency equipment is used. If 2 mm axial and lateral displacement is used, target (75) is laterally displaced by 2 mm from targets (73) and (77) and axially displaced by 4 mm from targets (73) and (77) since target (75) is axially displaced by 2 mm from targets (74) and (76). Again, the invention is not limited by the number of targets shown. As a group the targets can be moved up, down, front or back as required.

Scanning targets (81, 82, 83, 84 and 85) are used in determining the existence, location, intensity and width of side lobes substantially normal to the scanning plane. This determination occurs when the width of the ultrasonic beam is determined in a direction substantially normal to the scanning plane by moving the ultrasonic beam back and forth in the scanning plane centered above the cluster of scanning targets (71, 72, 73, 74, 75, 76, 77, 78 and 79). As a group, the targets (81, 82, 83, 84 or 85) should be positioned approximately where the location of a side lobe is predicted. From each other, the axial and lateral spacing of these targets will be similar to the axial and lateral spacing of targets (60, 61, 62, 63, 64, 65 and 66). Again, the number of targets is not limited, in any way, to the number of targets shown. Also, the targets can be moved up or down in the test object as required.

Figure 3:
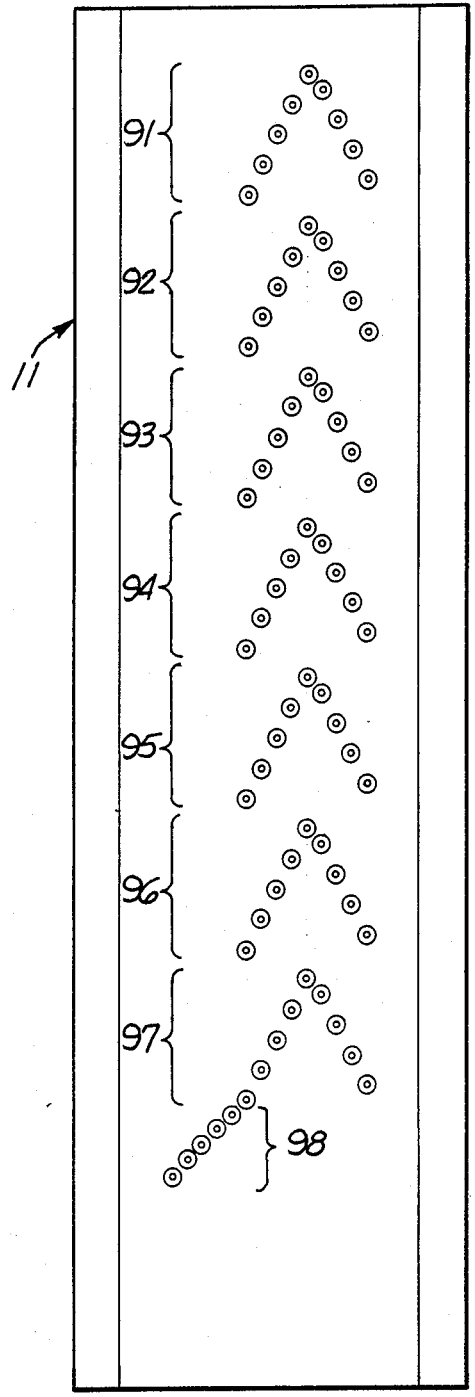
FIG. 3 is an end view of an alternative test object.

Referring to FIG. 3, clusters of scanning targets are shown in test object (11) to determine the width of the ultrasonic beam in a direction substantially normal to the scanning plane at various depths. Within each cluster the targets are used and positioned as previously described. While other configurations are possible using more or less clusters, more or less scanning targets in each cluster, or clusters at different distances from the transducer, the figure depicts nine scanning targets in each cluster. The top cluster (91) has scanning targets at varying distances from the transducer, not shown, from one to three centimeters. The targets of cluster (92) vary from three to five centimeters from the transducer. The same pattern of spacing is used for the targets of clusters (93, 94, 95, 96 and 97). The clusters can continue, as required, until the maximum usable depth of the transducer is obtained, currently about 20 cms. Also shown are the targets of cluster (98) used in the determination of the existence, location, intensity and width of side lobes in the direction substantially normal to the scanning plane as previously described. Cluster (98) need not be placed at the bottom of the test object. As required more scanning targets can be added to test object (11) for the determination of the characteristics of the ultrasonic beam.

FIG. 4 shows a wedge-shaped cluster of targets (100) similar to the wedge-shaped clusters of FIGS. 2 and 3 wherein the targets are formed by a cloth fabric made of nylon or other echogenic material having a suitable acoustic impedance mismatch with reference to the transmitting medium. The fabric is affixed to a wedge-shaped plastic support structure (102). The threads of the nylon cloth mesh are about 0.5 mm apart. Alternatively a wedged-shaped cluster of targets can be formed by coating the support structure (102) with echogenic particles such as graphite or the like having suitable acoustic, impedance mismatch with reference to the trasmitting medium. Positioned above the targets is a transducer assembly (112) aligned such that the scan plane (115) intersects the apex (116) and bisects the base (118) of the target wedge (100). Targets forming the apex of the wedge (100) will reflect the in-plane component of the beam, and will generate a well defined specular image representing the theoretical scan plane. Targets forming the sides (120) of the target wedge (100) will reflect the out-of-plane component of the beam at a plurality of ranges, and these echoes generate a diffuse band image whose height is proportional to the out-of-plane beam width at the range of the outermost reflecting targets. Preferably, the sides (120) of the wedge (100) diverge from the scan plane at equal and opposite angles of 26.6 degrees so that the base is equal to the height of the wedge. When the beam intersects the targets, an image is produced whose vertical height is equal to the width of the beam perpendicular to the scan plane.

Figure 5:
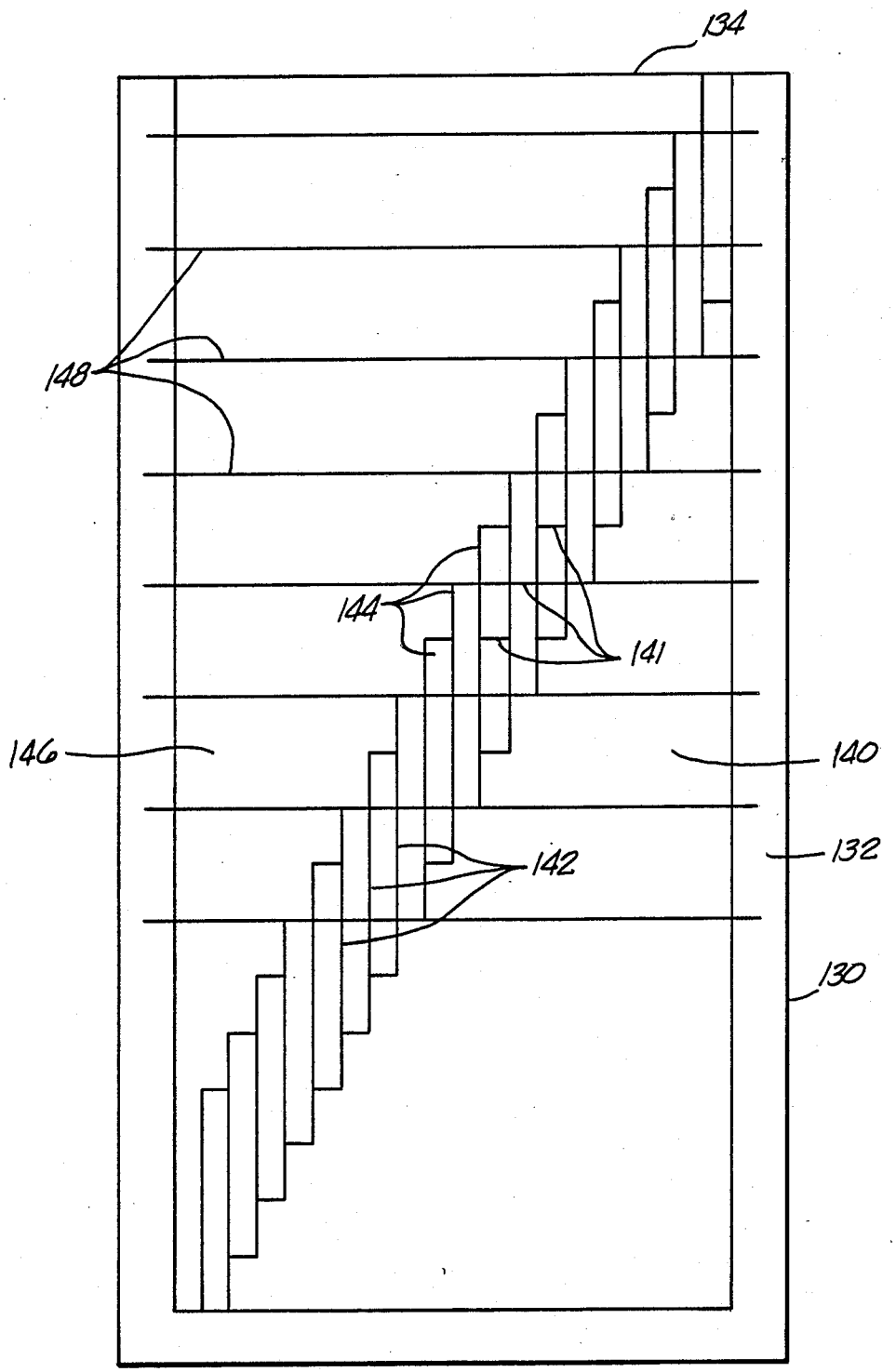
FIG. 5 is a side view of a test object constructed in accordance with the present invention looking perpendicular to the scanning plane showing multiple clusters of targets mounted on the steps of a step wedge platform.
Figure 6:
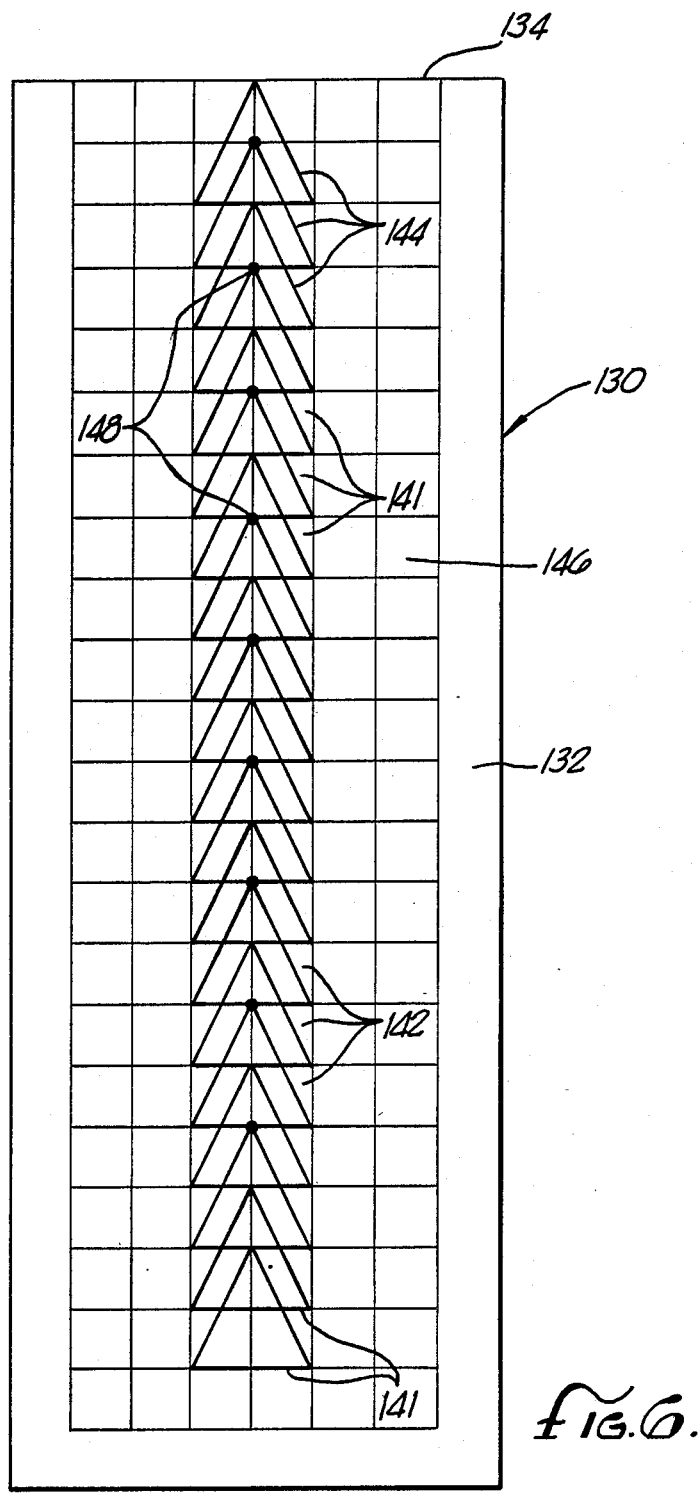
FIG. 6 is an end view of the object depicted in FIG. 5.

FIG. 5 depicts an arrangement whereby a detailed description of the out-of-plane beam shape may be obtained by placing wedge-shaped clusters of targets at appropriate ranges with the apices of the wedges aligned in the scan plane. A test object (130) comprises a frame (132) having a top (134), above which is positioned a transducer (not shown) generating a scan plane (not shown) parallel to the plane of the figure. Provided within the test object (130) is a step wedge platform (140) comprising a series of steps (141) and risers (142) upon which are mounted a plurality of wedge-shaped clusters of targets (144). Preferably the clusters (144) diverge from the scan plane in an amount sufficient to detect at least the first side lobe in a direction substantially normal to the scan plane. The test object (130) is filled with a tissue equivalent medium (146). Also positioned within the test object (130) are a series of ultrasonic guide wires (148) that are coincidental with the scan plane and positioned at depths of 1, 3, 5, 7, 9, 11, 13 and 15 cm respectively. The guide wires (148) are used for aligning the scan plane with the apices (150) of the wedges (144).

Figure 8:
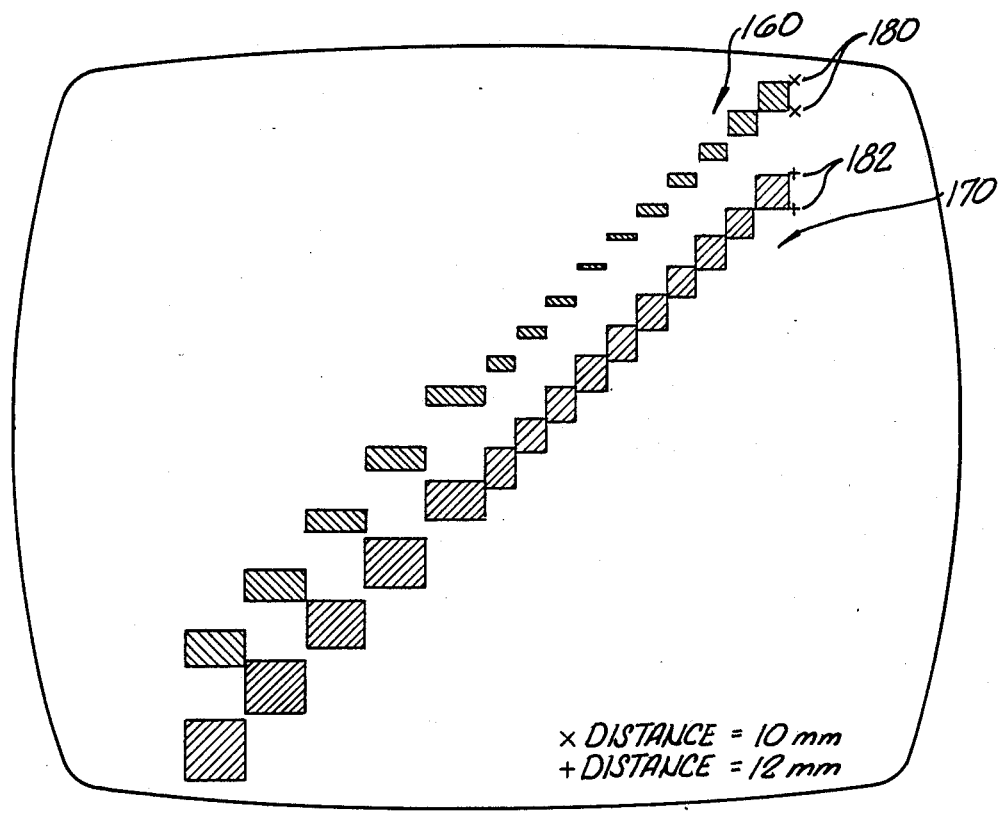
FIG. 8 is a front view of an image monitor showing a pair of electronic calipers (x,x) measuring the slice thickness of the beam at the level of the top target element and a second pair of electronic calipers (+,+) measuring the width of the first side lobe in the direction substantially normal to the scanning plane.

FIG. 8 depicts a typical scan obtained from the test object (130). The upper diagonal row of squares (160) represents the actual beam width as a function of depth. The lower diagonal row of squares (170) represents side lobes associated with the beam. A pair of electronic calipers (180) are shown measuring the out-of-plane beam width of the beam at the level of the top cluster of targets and a second pair of electronic calipers (182) are shown measuring the approximate width of the first side lobe in the direction substantially normal to the scan plane.

It should be understood that the above described embodiment is simply illustrative of the principles of this invention and numerous other embodiments may be readily devised by those skilled in the art without deviating therefrom. Therefore only the following claims are intended to define this invention.

What is claimed:

1. A test object for use in the testing and calibration of ultrasonic diagnostic equipment used in scanning a plane of tissue by emitting an ultrasonic beam comprising at least one scanning target positioned in the plane occupying an apex position and a plurality of subsequent scanning targets positioned adjacent the plane to form a wedge shaped cluster of scanning targets whose sides diverge from the plane over a range of depths to reflect at least some of the ultrasonic beam for determining the width of the ultrasonic beam in a direction substantially normal to the plane.

2. The test object of claim 1 wherein each subsequent scanning target is positioned at an increasing distance from the plane.

3. The test object of claim 2 wherein each scanning target is displaced from each other scanning target in the axial direction of the beam.

4. The test object of claim 3 wherein the axial displacement of each scanning target from each other scanning target is greater than the axial resolution of the ultrasonic diagnostic equipment being used.

5. The test object of claim 1 wherein the height and base of said wedge are equal.

6. The test object of claim 1 wherein the sides of the wedge diverge sufficiently from the plane to detect at least one side lobe in a direction substantially normal to the plane.

7. The test object of claim 1 wherein said scanning targets are formed by cylindrical rods.

8. The test object of claim 1 wherein said scanning targets are formed by a sheet of echogenic material.

9. The test object of claim 1 where said scanning targets are formed by echogenic particles.

10. A test object for use in the testing and calibration of ultrasonic diagnostic equipment used in scanning a plane of tissue by emitting an ultrasonic beam comprising a first scanning target positioned in the plane for determining the existence, location and intensity of a side lobe substantially in the direction of the plane and a second scanning target positioned adjacent to the plane for determining the existence, location and intensity of a side lobe substantially in the direction normal to the plane.

11. A test object for use in the testing and calibration of ultrasonic diagnostic equipment used in scanning a plane of tissue by emitting an ultrasonic beam comprising at least one scanning target positioned in the plane occupying an apex position and a plurality of subsequent scanning targets positioned adjacent the plane to form a wedge-shaped cluster of scanning targets whose sides diverge from the plane over a range of depths and whose height and base are equal, whereby the height of the image generated thereby is equal to the out-of-plane width of the beam.

* * * * *